United States Patent [19]

Hanson

[11] Patent Number: 4,698,017
[45] Date of Patent: Oct. 6, 1987

[54] ORTHODONTIC BRACKETS

[76] Inventor: Gustaf H. Hanson, 57 Augusta Street, Hamilton, Ontario, Canada, L8N 1P8

[21] Appl. No.: 940,142

[22] Filed: Dec. 10, 1986

[51] Int. Cl.$^4$ .............................................. A61C 7/00
[52] U.S. Cl. ......................................... 433/11; 433/13
[58] Field of Search ........................... 433/8, 10, 11, 21

[56] References Cited

U.S. PATENT DOCUMENTS

| | | | |
|---|---|---|---|
| 3,748,740 | 7/1973 | Wildman | 32/14 A |
| 4,171,568 | 10/1979 | Forster | 433/10 |
| 4,192,070 | 3/1980 | Lemchen et al. | 433/11 |
| 4,443,189 | 4/1984 | Wildman | 433/13 |
| 4,634,662 | 1/1987 | Rosenberg | 433/10 |

OTHER PUBLICATIONS

American Journal of Orthodontics, Mar. 1961, vol. 47, No. 3 Spring Rotation Bracket.

Primary Examiner—Robert Peshock
Attorney, Agent, or Firm—Rogers & Scott

[57] ABSTRACT

The invention provides a new orthodontic bracket consisting of a bracket body having a mesio-distal extending arch wire receiving slot that opens to the labial surface. A latch member of "comma" transverse cross-section is accommodated in a recess in the body, being pivoted thereto by two spaced pivot pins passing through the latch member body portion, while the latch member tail portion moves between a closed position in which it closes the arch wire slot to retain an arch wire therein, and an open position in which the arch wire can be inserted in and removed from the slot. A load spring for applying corrective forces to the arch wire is accommodated within the body to the lingual side of the slot and is a thin bowed sheet spring convex toward the latch so that it urges the arch wire toward the latch lingual surface, the gingival part of which is inclined lingually for cooperation with the arch wire in controlling the movements of the bracket on the arch wire. The latch preferably comprises a latch spring also accommodated within the body, and also a thin bowed sheet spring convex toward the latch member and engagable in the latch closed position with a mesio-distal detent ledge on the latch body; the latch spring is accessed for release of the latch by inserting a probe tool through a bore passing through the latch member.

12 Claims, 13 Drawing Figures

ORTHODONTIC BRACKETS

FIELD OF THE INVENTION

The present invention relates to new orthodontic brackets employed in procedures for applying corrective moving forces to teeth. The invention is concerned especially, but not exclusively, to such brackets intended for attachment directly to the tooth surfaces employing a suitable cement system.

REVIEW OF THE PRIOR ART

There have been a number of different proposals for orthodontic brackets that are fastened to the teeth and receive a connecting light springy arch wire without the use of ligating tie-wires to secure the arch wire to the brackets, and reference is made specifically to those disclosed in my prior U.S. Pat. Nos. 3,772,787, 4,248,588 and 4,492,573, issued respectively Nov. 20, 1973, Feb. 3, 1981 and Jan. 8, 1985, which constitute the Hanson "SPEED" system brackets now in use by many orthodontists. Such brackets employ a retainer member of thin sheet spring steel movable on a mesially-distally slotted body between open and closed positions in which respectively the labially-opening slot in the body is open to receive the arch wire, and closed to retain the arch wire, the springy retainer member engaging the arch wire to apply its spring force to the bracket and thereby to the tooth. There is a constant endeavour in this field to provide brackets that are as small and as smooth exteriorly as possible, both for cosmetic reasons, and also to reduce as much as possible rough contact of the brackets with the tongue and adjacent tissue of the patient's mouth, which can otherwise cause discomfort. There is also increasing interest in the so-called lingual technique in which the brackets are mounted on the lingual tooth surfaces, so that they are almost completely concealed, especially with adult patients who are particularly concerned with appearance during the two-three year period required for the average procedure. Small, smooth brackets are particularly needed for this location because of ready access by the tongue, and the natural tendency to explore any foreign object in the mouth with the tongue. However, if attempts are made to directly reduce the size of the existing brackets they become subject to the well known phenomenon that changes in scale do not affect all properties in the same ratio, e.g. areas decrease in square ratio and volumes decrease in cube ratio, with the result that it becomes difficult or impossible, especially with the spring members, to find materials of the required properties to maintain the necessary function.

DEFINITION OF THE INVENTION

It is therefore an object of the invention to provide a new orthodontic bracket of the tie-less, arch wire receiving type that is particularly suited for production in relatively small sizes.

It is another object to provide such a bracket in which spring members that are employed are concealed within the bracket and protected against over stressing.

According to the present invention there is provided an orthodontic bracket comprising:

a bracket body having lingual, labial, gingival, occlusal, distal and mesial surface portions and a mesio-distal extending arch wire receiving slot in the labial surface portion;

a latch member pivoted to the body about a mesio-distal extending pivot axis for movement between a closed position in which it extends in front of the labial mouth of the slot to retain an arch wire therein, and an open position in which an arch wire can be inserted in and withdrawn from the slot by labial or lingual movement thereof respectively;

a load spring disposed within the slot adjacent the lingual face thereof for engagement by an arch wire inserted in the slot to urge the arch wire labially against the latch member; and latch means operative between the bracket body and the latch member for latching the latch member in the said closed position.

DESCRIPTION OF THE DRAWINGS

Particular preferred embodiments of the invention will now be described, by way of example, with reference to the accompanying diagrammatic drawings, wherein.

DESCRIPTION OF THE PREFERRED EMBODIMENTS

Figure 1:
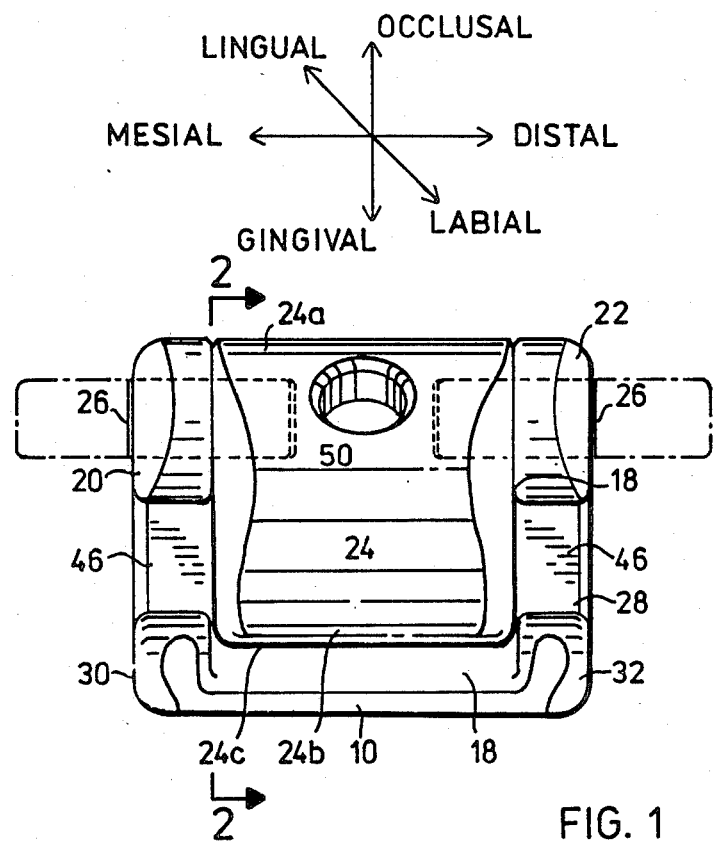
FIG. 1 is a front (labial) elevation of a complete bracket with the arch wire retaining latch member thereof in the closed position.
Figure 2:
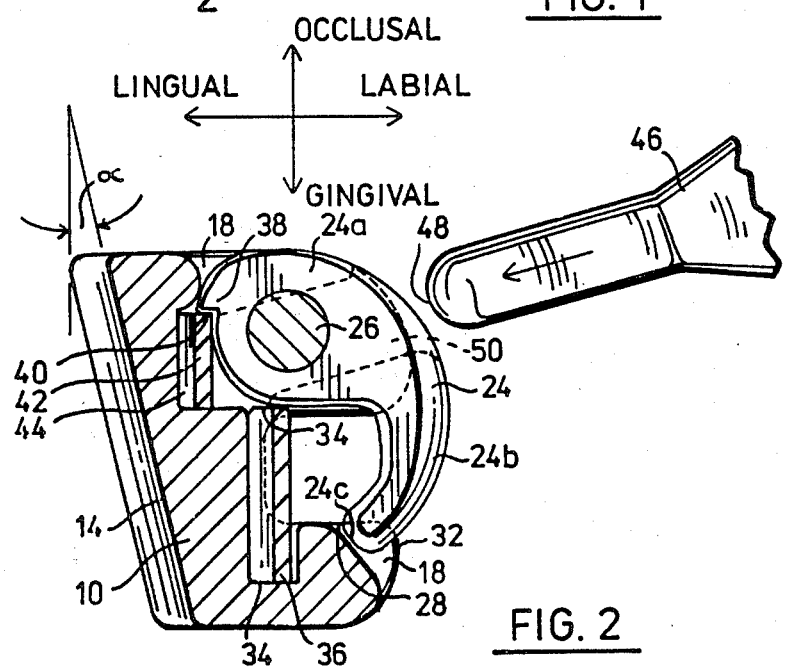
FIG. 2 is a cross-section (mesial view) taken generally on the line 2—2 of FIG. 1, but medially through the latch and load springs, and showing also a tool employed for unlatching the latch member.

In the description which follows and in the claims, for convenience in reference, the parts of the bracket will be referred to using the conventional directional nomenclature employed by orthodontists, with the bracket assumed to be mounted on the labial tooth surface, as is the case in the majority of the procedures that are undertaken at this time. The brackets of the invention are however particularly suited for use in lingual procedures, in which the brackets are instead mounted on the lingual tooth surfaces, so that they are concealed from view; with this latter technique, the lingual and labial directions are therefore reversed, and in addition, owing to the more extreme inclination on the lingual surfaces of upper incisors in the occlusal-gingival direction, the "labial" surfaces are designed so that the slot opens in the occlusal direction and a straight wire technique can be employed. FIGS. 1 and 2 each include a diagram to show the different designated directions. Moreover, since it is desired to make the external surfaces of the bracket as smoothly contoured as possible, immediately adjoining surface portions will usually merge with one another without a specific junction edge between them.

Figure 12:
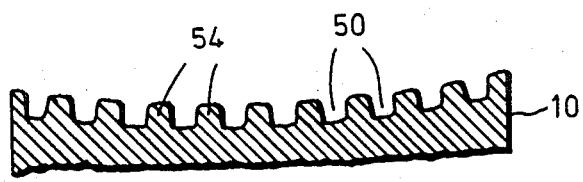
FIG. 12 is a part section taken on the line 12—12 of FIG. 11.
Figure 11:
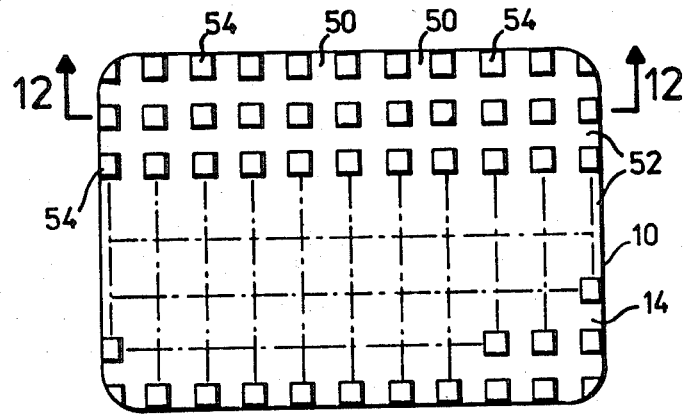
FIG. 11 is a rear (lingual) elevation of a bracket to show a preferred way of providing a cement receiving lingual surface thereon.

Each bracket comprises a body portion 10 which must be mounted on a respective tooth 12 (FIG. 6); in all of the embodiments illustrated herein this is done by cementing the lingual face 14 of the body directly to an acid etched surface of the tooth. Alternatively, as was the case before cementing systems were developed, and is still preferred by some orthodontists, the body can be attached to a tooth embracing band, but this is not illustrated. The lingual surface 14 of the body is therefore formed, for example as shown in FIGS. 11 and 12 and described in more detail below, to receive the cement by which the bracket is attached to the tooth surface. The surface is also shaped and angled as required in accordance with the inclination of the tooth and the contour of the tooth surface to which it is to be attached so as to facilitate the restorative action of a springy arch wire 16 to which the brackets are attached. For example, the embodiment illustrated by FIG. 2 has the lingual surface 14 concave curved toward the lingual direction in one plane and also inclined at angle α, which in this embodiment is about 12°; in practice this angle will vary from 0° to 24°. In the embodiment illustrated by FIG. 3 the surface 14 is concave curved in two directions at right angles to one another. The shaping and angles that are required for a complete set of brackets is well known to those skilled in this particular art and need not be described in further detail herein.

Figure 3:
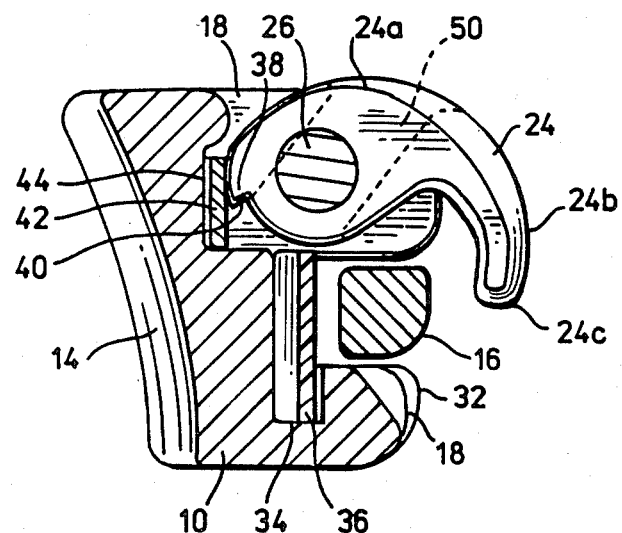
FIG. 3 is a mesial view cross-section as FIG. 2, but with the latch member in the open position.
Figure 4:
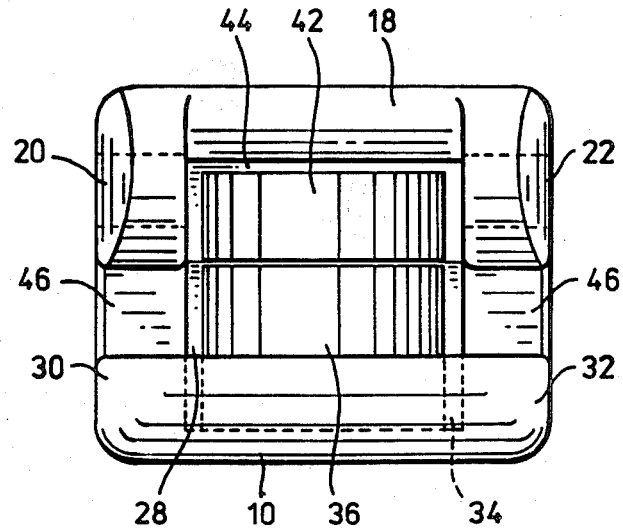
FIG. 4 is a front elevation of the bracket body corresponding to FIG. 1, but with the latch member removed for the latch and load springs to be seen.
Figure 5:
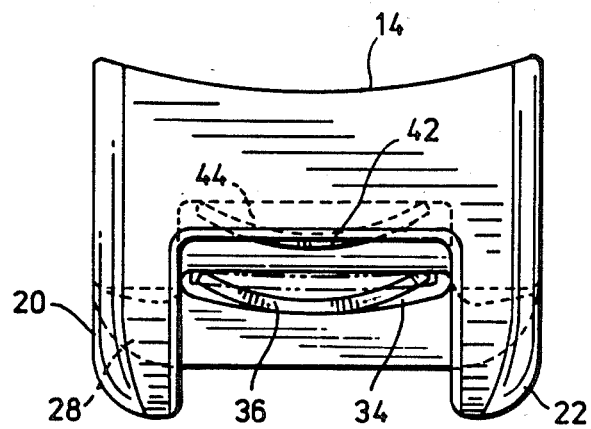
FIG. 5 is a top (occlusal) elevation of the bracket body, also with the latch member removed.

The body 10 is provided with a substantial recess 18 extending lingually and gingivally inwards respectively from its labial and occlusal surfaces so as to leave two spaced occlusal shoulders 20 (mesial side) and 22 (distal side) between which a latch member 24 is mounted for pivoting movement by two spaced coaxial pivot pins 26 between an open position illustrated for example by FIG. 3 and a closed position illustrated by FIG. 2. The body is also provided to the gingival side of the occlusal shoulders with a mesio-distal extending slot 28 which opens to the labial side for insertion of the arch wire therein. The shape of this slot 28 is best characterized as rectangular with rounded corners, as is best seen in FIG. 2. The recess 18 is continued beneath the slot 28 to form two gingival shoulders 30 and 32 in the respective portion of the body.

The body is further provided at the lingual side of the slot 28 with a load spring receiving recess 34 that extends gingivally beyond the slot 28, and also extends lingually deeper into the body than the arch wire slot so as to be able to receive and retain a thin curved rectangular load spring 36 which is formed to be convex in its longer dimension toward the labial opening of the arch wire slot, and so that a substantial portion of its body between its ends protrudes into the slot 28, the forward extent of this protrusion being determined by the engagement of its labial edges with the labial faces of the recess 34. The protrusion is also such that with arch wires of the cross-sections and dimensions that are usually employed, as illustrated by FIGS. 7(a) through 7(f), the latch member cannot be moved into and latched in its closed position without at least some contact of the arch wire with the spring, so that the spring urges the wire against the lingual face of the closed latch member. If the wire is not fully aligned within the slot then the spring is even more compressed with the latch closed, and the restoring spring force on the wire is correspondingly increased, the spring endeavouring to return to its position of least strain and applying a corresponding force to the wire, as will also be described below.

The latch member 24 in this embodiment can be described as of "comma" cross-section in the occlusal-gingival plane, with the body 24a of the comma receiving the pivot pins 26 perpendicular to that plane to permit the required pivoting movement, and with the "tail" 24b of the comma constituting the part that closes the labial mouth of the arch wire slot. The body 24a is provided in the portion of its face facing the bracket body with a mesio-distal extending detent 38 providing a gingival-facing ledge surface 40 engagable in the closed, latched position of FIG. 2 with a latch or detent spring 42 retained in a corresponding recess 44 in the bracket body. The latch spring 42 is of the same general configuration as the load spring 36, namely thin, rectangular and curved in its longer dimension to be convex toward the latch member. The curvature to which the spring 42 is normally set is such that in the closed position of the latch member its protruding occlusal edge engages beneath the ledge surface 42 and thereby prevents rotation of the latch member to the open position. The latch is released by pressing the spring in the lingual direction to flatten it into the recess 44 until the occlusal edge is freed from the detent 38; this is accomplished by use of a prod tool 46 (FIG. 2) having a rounded cylindrical end 48 which is pushed through a cylindrical bore 50 in the latch member, passing through it from the labial face to the part of the lingual face opposite the spring, until it engages the centre of the spring labial face. Two separate pivot pins 26 are employed to permit the passage of the tool at the required location.

The occlusal and labial faces of the latch member are smoothly convexly rounded in their respective directions, as are the shoulders 20, 22, 30 and 32, so as to avoid sharp edges as much as possible. The lingual surface of the latch tail 24b is overall generally concave in transverse cross-section (FIGS. 2 and 3), but with the part thereof toward the occlusal generally flat and, with the latch member in the closed position, as parallel as possible to the lingual face of the arch wire slot. The remaining part toward the gingival provides almost all of the concavity of this surface, and in this embodiment it is inclined at about 45° to the occlusal part, the lingual-labial spacing between it and the slot lingual face decreasing progressively toward the gingival. The extreme end 24c of the tail enters between the shoulders 30 and 32 and has its face generally parallel to the adjacent face of the bracket body. It will be seen that with this shape of the latch member the effective cross-section of the arch wire slot with the latch closed corresponds most closely with that of the arch wires illustrated in FIGS. 7(a) and 7(f). The latch can be closed by rotation by hand against the force of the load spring 36 until the tooth spring 42 snaps beneath the detent 38. If desired for convenience this movement can be effected by use of the tool 46 engaged in the bore 50, but this is not usually required for leverage purposes since the forces involved are so small.

It is found with my new bracket that it is possible to make it considerably smaller even than my own prior bracket. Thus, typically one of my prior brackets measures 3.38 mm (0.133 in.) in the occlusal-gingival direction; 3 mm (0.140 in.) in the mesio-distal direction, and about 1.90 to 0.22 mm (0.075 to 0.093 in.) in the lingual-labial direction, the lastmentioned dimension varying in dependence upon the tooth to which it is to be applied and consequently the contour, etc. of the lingual face. A bracket of the present invention can be made with an occlusal-gingival dimension, which is the most important for consideration of bracket size in order to reduce tongue irritation, of about 1.93 mm (0.076 in.) and a mesiodistal dimension of 2.59 mm (0.102 in.). The lingual-labial dimension will also vary in the range 1.47 to 1.93 mm (0.058 to 0.076 in.), depending upon the tooth involved. As described above built-in torque can be achieved by varying the angle α of the lingual surface, avoiding the need with my prior bracket to angle the slot for this purpose. This has the effect that the sliding friction of the wire in the different brackets will remain more constant from bracket to bracket. The material employed will be any of the usual hard, tough, corrosion resistant alloys used for orthodontic brackets in the hostil environment of the human mouth.

In this embodiment the load spring is 1.37 mm (0.054 in.) in length (mesio-distal); 0.91 mm (0.036 in.) in height (occlusal-gingival) and is 0.063 mm (0.0025 in.) thick (lingual-labial) and unconstrained prior to assembly is formed to a radius of 0.76 mm (0.030 in.). Its radius within the pocket will be of the order of 1.27 mm (0.050 in.). The modulus of the material is such that a force of about 2-10 ozs will flatten the spring against the supporting back surface. The latch spring is 1.37 mm (0.054 in.) in length; 0.48 mm (0.019 in.) in height, and of the same thickness, the same material and formed to the same radius. It will be seen that both of the springs are completely concealed and shielded, with no possibility that they can be constrained beyond their elastic limit in operation, since this involves movement lingually into contact with a solid wall that will prevent excessive motion. There is the possibility of overstressing during assembly, as the springs are bowed to place them in their respective recesses, but only because of gross carelessness by a human operator or mechanical malfunction by an automatic assembler.

Figure 6:
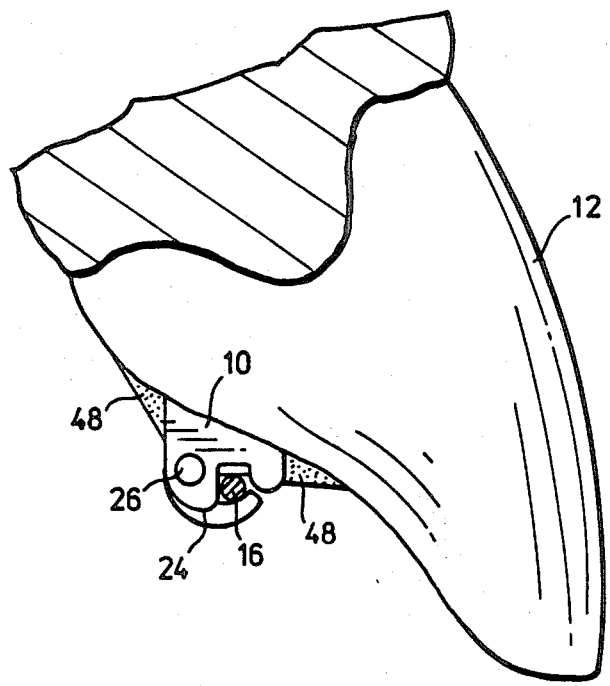
FIG. 6 is a side elevation showing a central incisor tooth and a bracket of the invention cemented to the lingual surface thereof, as in the so-called lingual technique.

In some embodiments the two pivot pins 26 may protrude respectively mesially and distally beyond the bracket body, as indicated in broken lines in FIG. 1, to provide anchors for elastics when these are required. FIG. 6 illustrates the application of brackets of the invention to lingual procedures, in which the brackets are fastened to the lingual tooth surfaces. The tooth illustrated is one of the central incisors and the relative sizes of the tooth and the bracket will be seen; the profile of the lingual surface of such a tooth is commonly so extreme that, as illustrated, the bracket surface that is the labial in the more usual labial procedure is in this application facing occlusally.

Figure 7A:
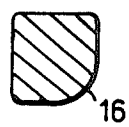
FIGS. 7(a) through 7(f) show different cross-sections of arch wire suitable for use with the brackets of the invention.
Figure 7B:
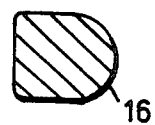
Figure 7C:
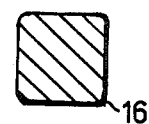
Figure 7D:
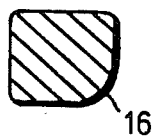
Figure 7E:
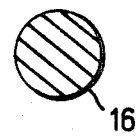

FIGS. 7(a) through 7(f) show the cross-sections of various wires that may be used with the brackets of the invention. FIGS. 7(c) and 7(e) show respectively the square and circular cross-sections that are commonly employed, while FIGS. 7(a), 7(b), 7(d) and 7(f) show wires that are configured specially to cooperate with the concave lingual surface of the latch tail by having the junction between the labial and gingival faces smoothly convexly curved, the cross-sections 7(b) and 7(f) being additionally symetrically rounded at the occlusal-labial junction. The symmetrical wires of FIGS. 7(b) and 7(f) permit the brackets, when used in a labial technique, to be inverted so that excessive bulk can be avoided in providing the necessary built-in torque. In this embodiment the arch wire slot has an effective occlusal-gingival dimension of 0.56 mm (0.022 in.) and a lingual-labial dimension adjacent the occlusal slot face with the load spring unstressed of 0.46 mm (0.018 in.). This will just accommodate the round wire of FIG. 7(e), which is of 0.46 mm (0.018 in.) diameter and the wires of FIGS. 7(a) and 7(f) of corresponding dimensions. The "square" wire of FIG. 7(c) will cause stressing of the load spring because of the engagement of its labial-gingival junction with the latch member, while the wires of FIGS. 7(b) and 7(d) will also cause stressing because of their increased labial-lingual dimension to 0.52 mm (0.020 in.), or even to as much as 0.56 mm (0.022 in.), which will compress the spring and increase the friction between the wire and the bracket.

Reference is now made specifically to FIGS. 5, 8, 9 and 10 to illustrate some of the actions that are possible with the brackets of the invention. From FIG. 5 it will be seen that the lingual walls 46 of the arch wire slot 28 between the pairs of shoulders 20 and 30, 22 and 32 are not flat, but are shaped on a radius in a plane containing the mesial, distal, occlusal and gingival directions to progressively protrude into the slot toward the central recess 18; the surfaces therefore conform to the most usual shape of the portion of the arch wire passing through the bracket, in that most of the wire is curved to conform to the arch of the teeth and only the portion associated with the rear molars is relatively straight.

Figure 8A:
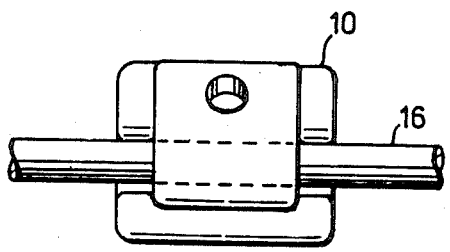
FIGS. 8(a) and 8(b) are respectively front and side elevations of a bracket with a round arch wire mounted therein and in a neutral position.
Figure 8B:
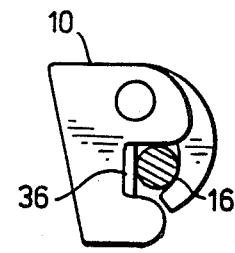
Figure 9A:
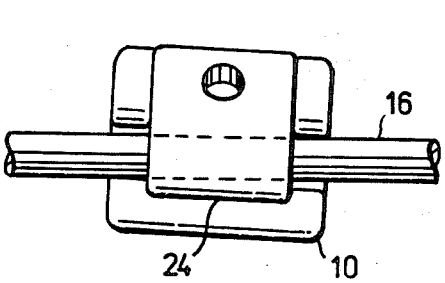
FIGS. 9(a) and 9(b) are respectively views similar to FIGS. 8(a) and 8(b) and showing the result of tilting the bracket relative to the wire.
Figure 9B:
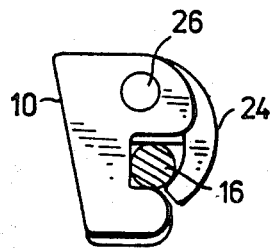
Figure 10A:
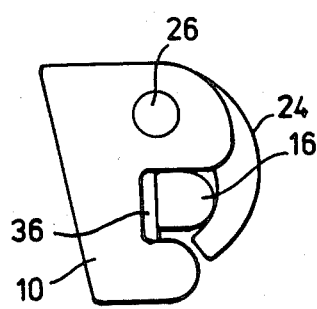
FIGS. 10(a) through 10(c) show, by way of example, the way in which the arch wire of cross-section shown in Figure 7(f) cooperates with the bracket to produce tilting of the tooth to which it is attached.
Figure 10B:
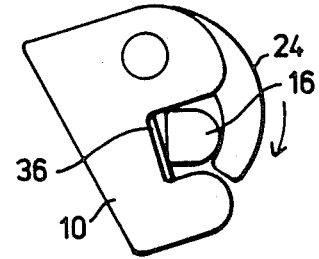
Figure 10C:
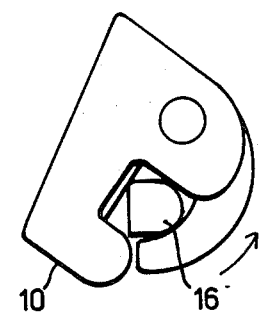

It is essential in orthodontic practice for the brackets to be able to slide along the wire to permit the corresponding tooth displacement, and for this to take place there must be sufficient clearance between the wall of the slot and the surfaces of the wires which are used. It is also important that this displacement take place without lagging of the root portion, which results in tilting of the tooth in its direction of movement. The manner in which brackets of the invention operate to prevent such tilting is illustrated by FIGS. 8(a), 8(b), 9(a) and 9(b). Thus, FIGS. 8(a) and 8(b) show the situation when the bracket is perpendicular to the wire, whereupon the wire is in the labial-occlusal corner of the arch wire slot and the load spring is in its position of least stress. If the crown of the tooth moves in advance of or behind the root then the bracket tilts on the wire, as illustrated by FIGS. 9(a) and 9(b), whereupon the load spring is compressed; the attempt by the spring to return to the position of least stress applies the necessary corrective rotation to the bracket and hence to the tooth. It will also be noted that the bracket must rotate about the occlusal-gingival axis because of the engagement of the wire with the inclined portion of the latch lingual surface, which will also counter the natural tendency of the opposite portion of the tooth to lag in its original position. The bracket in combination with a round wire is therefore able to control tilting in the occlusal-gingival plane, as well as rotation in the labial-lingual plane, but not tipping in the occlusal-gingival plane (i.e. about the wire longitudinal axis). Control in all three directions, including the last-mentioned occlusal-gingival plane, can be achieved by use of one of the wires of non-circular cross-section as illustrated by FIGS. 10(a) through 10(c). FIG. 10(a) shows the neutral position with the bracket and tooth "untipped", while FIG. 10(b) shows that when the bracket is tipped lingually the load spring is stressed and the restoring force (indicated by the arrow) acts labially, and FIG. 10(c) shows that a lingually-acting restoring force is provided when the tooth is tipped labially.

FIG. 6 also shows that the shape of the brackets of the invention is such that they can be surrounded at their junction with the tooth with an excess of the cement 48 to provide a smooth contoured body that is less irritating to the tongue. A preferred configuration for the tooth-engaging surface is illustrated by FIGS. 11 and 12, namely wherein two sets or pluralities of parallel grooves 50 and 52 at right angels to one another are formed in the face to result in a multiplicity of square pillars 54 that engage the tooth surface. The cement can enter readily into the grooves and the surplus exit at their ends as the bracket is pressed against the tooth to provide the cement surround illustrated by FIG. 6. Such a structure can be produced directly in the bracket body, e.g. by casting or powder metallurgy, and avoids the need for a secondary operation to attach a foil mesh or coated foil to act as a bonding base.

Figure 7F:
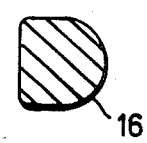
Figure 13:
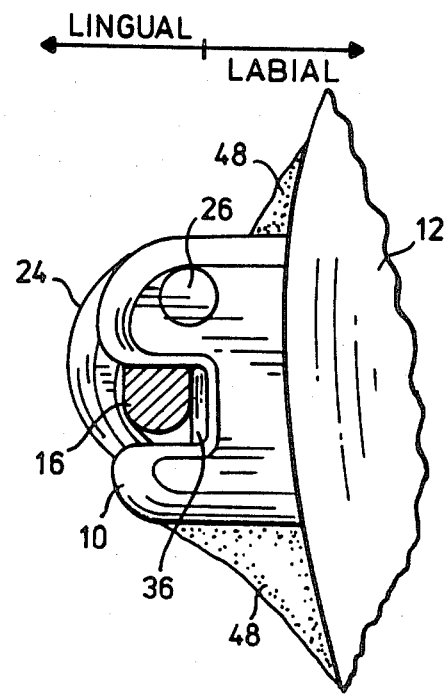
FIG. 13 is a side elevation similar to FIG. 6 to show the use of a bracket with a different orientation of the wire relative to the slot.

FIG. 13 shows a mesial view of a bracket mounted on the lingual surface of a second bicuspid tooth employing a wire of the cross-section shown in FIG. 7(f). At this tooth location, if a "straight" wire technique is to be employed, the half round side of the wire is directed toward the occlusal, and the bracket will accept lingual entry into the slot, which is the only practical way for the bicuspids and molars, without significant loss of attitude control.

I claim:

1. An orthodontic bracket comprising:
   a bracket body having lingual, labial, gingival, occlusal, distal and mesial surface portions and a mesiodistal extending arch wire receiving slot in the labial surface portion;
   a latch member pivoted to the body about a mesiodistal extending pivot axis for movement between a closed position in which it extends in front of the labial mouth of the slot to retain an arch wire therein, and an open position in which an arch wire can be inserted in and withdrawn from the slot by labial or lingual movement thereof respectively;
   a load spring disposed within the slot adjacent the lingual face thereof for engagement by an arch wire inserted in the slot to urge the arch wire labially against the latch member; and
   latch means operative between the bracket body and the latch member for latching the latch member in the said closed position.

2. An orthodontic bracket as claimed in claim 1, wherein the load spring is a thin curved sheet spring member having parallel convex and concave surfaces and disposed against a lingual face of the slot with its convex surface facing the lingual face of the latch member, the load spring being additionally stressed by engagement with the arch wire that flattens it toward the said slot lingual face.

3. An orthodontic bracket as claimed in claim 2, wherein the gingival edge portion of the spring member is contained in a slot extending gingivally from the gingival surface of the arch wire slot and opening to the slot gingival surface to retain the member in the arch wire slot for required engagement with the arch wire.

4. An orthodontic bracket as claimed in claim 1, wherein the latch means comprises a mesio-distal extending detent ledge on the latch member, and a latch spring interposed between the bracket body and the latch member to engage the detent ledge and hold the latch member latched in the said closed position.

5. An orthodontic bracket as claimed in claim 4, wherein the latch spring is a thin curved sheet spring member having parallel convex and concave surfaces and disposed against a lingual face of the bracket body with its convex face facing the latch member, the latch spring being moved toward the bracket body lingual face to disengage it from the latch member detent ledge and to release the latch member to move to the said open position.

6. An orthodontic bracket as claimed in claim 5, wherein the latch member has therein a bore through which the latch spring is engaged by a tool to disengage it from the latch member detent edge.

7. An orthodontic bracket as claimed in claim 6, wherein the latch member is pivoted to the bracket body by two transversely spaced coaxial pivot pins, and the said bore passes between the facing ends of the pivot pins.

8. An orthodontic bracket as claimed in claim 1, wherein the latch member is of "comma" cross-section in the occlusal gingival plane having a body portion and tail portion, pivot means pivoting the member to the bracket body passing into the body portion, and the tail portion closing the arch wire slot when the latch member is in the closed position.

9. An orthodontic bracket as claimed in claim 8, wherein with the latch member in the closed position the lingual face of the latch member tail portion has the occlusal part thereof at least approximately parallel to the slot lingual face, and the gingival part thereof extending at an angle to the occlusal part toward the slot lingual face.

10. An orthodontic bracket as claimed in claim 9, wherein the gingival part of the lingual face of the latch member tail portion extends at about 45° to the occlusal part of the same face.

11. An orthodontic bracket as claimed in claim 1, wherein the portions of the lingual face of the arch wire slot on both sides of the latch member are formed on a radius to be convex toward the labial to conform with the curvature of an arch wire in the slot.

12. An orthodontic bracket as claimed in claim 1, wherein the lingual face of the bracket body is provided with two sets of grooves for reception of cement for attaching the bracket to a tooth, the grooves of each set being parallel to one another, the grooves of one set being transverse to the grooves of the other set to form residual pillars between them.

* * * * *